US005554382A

United States Patent [19]
Castor

[11] Patent Number: 5,554,382
[45] Date of Patent: Sep. 10, 1996

[54] METHODS AND APPARATUS FOR MAKING LIPOSOMES

[75] Inventor: Trevor P. Castor, Arlington, Mass.

[73] Assignee: Aphios Corporation, Woburn, Mass.

[21] Appl. No.: 69,134

[22] Filed: May 28, 1993

[51] Int. Cl.$^6$ .............. A61K 9/127; A61K 9/133; B01J 13/12; B28B 1/54

[52] U.S. Cl. .............. 424/450; 264/4.1; 264/4.3; 264/4.6; 424/45; 425/5

[58] Field of Search .............. 264/4.1, 4.3, 4.6; 436/829; 425/5; 424/45, 450

[56] References Cited

U.S. PATENT DOCUMENTS

| | | | |
|---|---|---|---|
| 4,508,703 | 4/1985 | Redziniak et al. | 424/450 |
| 4,608,211 | 8/1986 | Handjani et al. | 264/4.6 |
| 4,752,425 | 6/1988 | Martin et al. | 264/4.6 |
| 5,088,499 | 2/1992 | Unger | 424/450 X |
| 5,141,674 | 8/1992 | Leigh | 252/305 |
| 5,192,528 | 3/1993 | Radhakrishnan et al. | 424/45 |
| 5,348,016 | 9/1994 | Unger et al. | 264/4.6 X |

FOREIGN PATENT DOCUMENTS

| | | |
|---|---|---|
| 190926 | 8/1986 | European Pat. Off. . |
| 338971 | 10/1989 | European Pat. Off. . |
| 8601714 | 3/1986 | WIPO . |
| 8707502 | 12/1987 | WIPO . |
| 8801864 | 3/1988 | WIPO . |

OTHER PUBLICATIONS

McCafferty, Frank D., The Encapsulation Of Food Additives In Liposomes, Jun. 1990, pp. 1–121, Massachusetts Institute of Technology©.

*Primary Examiner*—Richard D. Lovering
*Attorney, Agent, or Firm*—Wolf, Greenfield & Sacks, P.C.

[57] ABSTRACT

The present application features methods and apparatus for making liposomes with critical, supercritical or near critical fluids. The methods and apparatus combine a phospholipid and an aqueous phase, or multilamellar vesicles, with a critical, supercritical or near critical fluid. Upon a reduction in pressure, liposomes are formed.

31 Claims, 6 Drawing Sheets

METHODS AND APPARATUS FOR MAKING LIPOSOMES

FIELD OF THE INVENTION

This invention relates generally to methods and apparatus for making liposomes. The methods and apparatus feature critical, supercritical, or near critical fluids.

BACKGROUND OF THE INVENTION

Liposomes are microscopic vesicles comprised of single or multiple phospholipid bilayers which can entrap hydrophilic compounds within their aqueous cores. Liposomes have been formed in sizes as small as tens of Angstroms to as large as a few microns. Most liposomes are non-toxic, non-antigenic and biodegradable in character since they have the molecular characteristics of mammalian membranes.

Liposomes are used as carriers for drugs. Liposomes can be made with different features which can enhance a drug's efficacy; reduce a drug's toxicity; and prolong the drug's therapeutic effect.

Liposomes with multiple bilayers are known as multilamellar vesicles (MLVs). MLVs are excellent candidates for time release drugs because the fluids entrapped between layers are only released as each membrane degrades. Liposomes with a single bilayer are known as unilamellar vesicles (UV). UVs may be made extremely small (SUVs) or large (LUVs).

Liposomes are prepared in the laboratory by sonication, detergent dialysis, ethanol injection, French press extrusion, ether infusion, and reverse phase evaporation. These methods often leave residuals such as detergents or organics with the final liposome. From a production standpoint, it is clearly preferable to utilize procedures which do not use organic solvents since these materials must be subsequently removed.

Some of the methods impose harsh or extreme conditions which can result in the denaturation of the phospholipid raw material and encapsulated drugs. These methods are not readily scalable for mass production of large volumes of liposomes.

Several methods exist for producing MLVs, LUVs and SUVs without the use of organic solvents. MLVs, free of organic solvents, are usually prepared by agitating lipids in the presence of water. The MLVs are then subjected to several cycles of freeze-thawing in order to increase the trapping efficiencies for water soluble drugs. MLVs are also used as the starting materials for LUV and SUV production.

One approach of creating LUVs, free of organic solvents, involves the high pressure extrusion of MLVs through polycarbonate filters of controlled pore size. SUVs can be produced from MLVs by sonication, French press or high pressure homogenization techniques. High pressure homogenization has certain limitations. High pressure homogenization is useful only for the formation of SUVs. In addition, high pressure homogenization may create excessively high temperatures. Extremely high pressures are associated with equipment failures. High pressure homogenization does not insure end-product sterility. High pressure homogenization is associated with poor operability because of valve plugging and poor solution recycling.

The use of liposomes for the delivery and controlled release of therapeutic drugs requires relatively large supplies of liposomes suitable for in vivo use. Ostro, M. J. and Cullis, P. R., "Use of Liposomes as Injectable Drug Delivery Systems", *American Journal of Hospital Pharmacy*, 46:1576–1587 (1989). Present laboratory scale methods lack reproducibility, in terms of quantity and quality of encapsulated drug, lipid content and integrity, and liposome size distribution and captured volume. The multidimensional characteristics of the drug and the liposome, as well as potential raw material variability, influence reproducibility.

Present liposome products are not stable. It is desirable to have final formulations which are stable for six months to two years at room temperature or refrigeration temperature. Stability requirements have been relaxed by techniques for dehydrating liposomes. Dehydrated liposomes can be distributed to hospitals free of drugs and mixed with the drug immediately prior to use by a hospital pharmacist. However, compounding of the liposome containing drug by a pharmacist increases the cost of the therapy and adds further potential for compounding errors.

Present liposome products are difficult to sterilize. Sterility is currently accomplished by independently sterilizing the component parts—lipid, buffer, drug and water—by autoclave or filtration and then mixing in a sterile environment. This sterilization process is difficult, time consuming and expensive since the product must be demonstratively sterile after several processing steps.

Heat sterilization of the finished product is not possible since heating liposomes does irreparable damage to liposomes. Filtration through 0.22 micron filters may also alter the features of multilayered liposomes. Gamma ray treatment, not commonly used in the pharmaceutical industry, may disrupt liposome membranes. Picosecond laser sterilization is still experimental and has not yet been applied to the sterilization of any commercial pharmaceutical.

There exists a need for large scale cost effective liposome manufacturing processes which can meet the growing market demand for liposomal drug delivery and controlled release vehicles. The process and equipment should recycle unentrapped drugs, lipids and solvents. The process and equipment should produce uniform liposome products. The ability to operate continuously is an added benefit to the process.

SUMMARY OF THE INVENTION

The present invention features methods and apparatus for producing liposomes. The methods and apparatus are suitable for large scale production of pharmaceutical grade liposomes which are sterile, of a predetermined size, and are substantially free of organic solvents.

The present invention features several different methods of making liposomes using critical, supercritical or near critical fluids.

As used herein, the term "phospholipid" refers to compositions which are esters of fatty acids in which the alcohol component of the molecule contains a phosphate group as an integral part. Phospholipids comprise the glycerophosphatides, containing glycerol, and the sphingomyelins containing sphingosine.

In the field of physical chemistry, the term "critical fluid" refers to a gas at its critical temperatures and at its critical pressures. The term "supercritical fluid" refers to a gas above its critical temperature and above its critical pressure. Supercritical fluids are sometimes designated in this application by the abbreviation "SCF". The term "near critical" is used in the sense of approaching or close to being critical. One example, without limitation, of a near critical fluid is a gas having a temperature below its critical temperature and a pressure at or above the critical pressure. Such gas has properties which, may approach those of a supercritical or critical fluid, particularly in solvating properties.

In industrial settings where critical, supercritical and near critical fluids are used, it is common, particularly where the solvent properties are being applied, to use the term "critical" to refer to supercritical, critical and near critical fluids. This application will use the term "SCoCoNC fluid" to represent supercritical, critical or near critical fluids. The use of the term "critical" with respect to liposomes and liposome formation refers to liposomes formed with supercritical fluid and near critical fluids as well as critical fluid. Fluids are sometimes referred to in the examples as "critical" as a convenience, even though such fluids may be supercritical, critical or near critical.

Solvating properties of SCoCoNC fluids are influenced by cosolvents and entrainers. The terms cosolvents and entrainers are used interchangeably to suggest compositions which are soluble in the SCoCoNC and impart desirable solubility features to the SCoCoNC to which they are added with respect to phospholipids and aqueous phases. Nonpolar cosolvents refer to compositions having no or slight dipole moment, ranging approximately from 0.0 to 0.1 Debyes. Polar cosolvents refer to compositions having a dipole moment, ranging approximately from 0.1 to 1.7 Debyes.

As used herein, the term "aqueous phase" refers to a composition comprising in whole, or in part, water.

Preferably, the SCoCoNC fluid is selected from the group of compositions capable of forming critical fluids comprising carbon dioxide; nitrous oxide; halo-hydrocarbons, such as FREON; alkanes such as propane and ethane; and alkenes, such as ethylene.

In the present method, the rate of depressurization influences the size of the liposome formed.

One method comprises the steps of forming a solution or mixture of a phospholipid, an aqueous phase and a critical, supercritical or near critical fluid. The solution or mixture is decompressed to separate the critical, supercritical or near critical fluid, from the phospholipid and aqueous media, to form one or more liposomes.

In some embodiments, the aqueous phase has a therapeutic agent. As used herein, the term "therapeutic agent" means a chemical or drug capable of effecting a desirable response in an individual subject. This embodiment of the present invention is ideally suited for therapeutic agents which are not shear sensitive.

Preferably, a mixture of the aqueous phase and a solution of the phospholipid in a SCoCoNC fluid is held in a chamber of a first vessel. The solution or mixture is then decompressed as the solution passes to a second chamber or a second vessel. The second chamber allows the SCoCoNC fluid to be removed from the liposome compositions formed.

Preferably the SCoCoNC fluid is recycled. To the extent that phospholipids and aqueous phase are carried over with the SCoCoNC fluid, such components may also be recycled. For convenience, liposomes formed with SCoCoNC fluid are referred to as "critical fluid liposomes" or "CFLs".

One embodiment of the present invention features an apparatus for forming liposomes. The apparatus comprises a first vessel wherein a phospholipid, an aqueous phase and a SCoCoNC fluid are combined to form a mixture or solution. The apparatus further comprises a second vessel in communication with the first vessel. The apparatus further comprises depressurization means capable of reducing the pressure of the solution or mixture. Depressurization means may be interposed between the first and second vessels or may be integral with the second vessel. The second vessel receives the solution or mixture of phospholipids and an aqueous phase which form liposomes upon depressurization.

Preferably, SCoCoNC fluid is removed from depressurization means and/or the second vessel and recycled.

One embodiment of the present invention comprises the steps of forming a solution or mixture of a phospholipid and a SCoCoNC. The solution or mixture is then decompressed through a tip or orifice into an aqueous phase to form one or more liposomes. As a result of the decompression, the SCoCoNC fluid is separated from the phospholipids and the aqueous phase. The released SCoCoNC is either vented or recycled to form a solution or mixture of phospholipid.

A further embodiment of the present invention features a method of making liposomes comprising the steps of forming a solution or mixture of a phospholipid and a SCoCoNC fluid. The solution or mixture is injected into an aqueous phase to form one or more liposomes as the phospholipids and SCoCoNC fluids are decompressed.

Preferably, the aqueous phase or phospholipids contain a therapeutic agent which is incorporated into the liposome. Embodiments of the present method are ideally suited for therapeutic agents which are shear sensitive such as proteins and peptides. Embodiments of the present method do not subject proteins and peptides to extreme shear forces or temperatures.

Embodiments of the present method are ideally suited to form unilamellar liposomes. The size of the liposome is determined by the rate of decompression.

A preferred method uses a SCoCoNC fluid selected from the group of compositions capable of forming a critical fluid comprising carbon dioxide; nitrous oxide; halo-hydrocarbons, such as FREON; alkanes such as propane and ethane; and alkanes such as ethylene.

One embodiment of the present invention features an apparatus for forming liposomes. The apparatus comprises a first vessel for containing a solution or mixture of a phospholipid and a SCoCoNC fluid. The apparatus further comprises a second vessel for containing an aqueous phase. The first vessel and the second vessel are in communication by means of injection means for injecting the phospholipid and SCoCoNC fluid mixture into the aqueous phase. Upon injection into the aqueous phase, liposomes are formed.

Preferably, the aqueous phase contains a therapeutic agent which therapeutic agent is encapsulated within the liposome.

SCoCoNC fluid is released from the phospholipid upon injection and decompression into the aqueous phase. Preferably, the SCoCoNC fluid is recycled to the first vessel to form additional solutions or mixtures of phospholipid and SCoCoNC fluid.

In another embodiment of this invention, a solution or mixture of the phospholipid and therapeutic agent is first made in a SCoCoNC fluid, decompressed, and injected into an aqueous buffer or phase. It should be noted that the phospholipids and therapeutic agent can be individually or collectively mixed with the SCoCoNC fluids This method is particularly well suited for the liposome encapsulation of hydrophobic drugs such as certain anti-cancer compounds including but not limited to taxol, camptothecin, cisplatin, doxorubicin, etc.

A further embodiment of the present invention features a method of making liposomes comprising forming a mixture of multilamellar vesicles and a SCoCoNC fluid. The mixture is decompressed to remove the SCoCoNC fluid to form one or more liposomes Preferably, multilamellar vesicles are made by hydrating phospholipids in an aqueous phase. Preferably, the aqueous phase or the phospholipids contain a therapeutic agent.

The size of the liposome can be controlled by the rate of decompression to form liposomes of predetermined size.

One embodiment of the present invention features an apparatus for forming liposomes. The apparatus comprises a first vessel for containing a mixture of muiltilamellar vesicles and a SCoCoNC fluid. The first vessel is in communication with a second vessel which second vessel is capable of decompressing the mixture to remove the SCoCoNC fluid. During decompression, one or more liposomes are formed.

One embodiment of the present invention further comprises a third vessel for forming multilamellar vesicles by hydrating phospholipids in an aqueous phase. The aqueous phase or the phospholipids may contain a therapeutic agent to impart special qualities to the liposome.

An embodiment of the present invention further features control means for determining the rate of decompression. The rate of decompression determines the size of liposomes.

Preferably, SCoCoNC fluid removed from the liposome preparation in the decompression vessel is recycled to the first vessel to form additional mixtures of multilamellar vesicles and SCoCoNC fluid.

Contact with SCoCoNC fluid may cause destruction of the cellular structures particularly upon rapid decompression. Thus, embodiments of the present invention are, for the most part, self-sterilizing.

Methods and apparatus of the present invention are capable of forming liposomes which carry a therapeutic agent. The therapeutic agent can be incorporated into ingredients which are used to form the liposome or the liposome can be loaded with the therapeutic agent after the liposome is formed in a manner known in the art.

Embodiments of the present invention allow the recovery of raw materials, lipids and solvents which are not incorporated into the final liposome product. Embodiments of the present invention feature efficient drug entrapment and recovery of unencapsulated drugs. The operating parameters of the apparatus and method are consistent with other industrially applied processes. The method and apparatus are capable of operating continuously.

These and other advantages will be apparent to individuals skilled in the art in view of the drawings and detailed description which follow.

DETAILED DESCRIPTION OF THE DRAWING

The present invention will be described in detail as a method and apparatus for forming liposomes. The method and apparatus have applications for drug delivery, pharmaceutics, cosmetics, and food processing.

Figure 1:
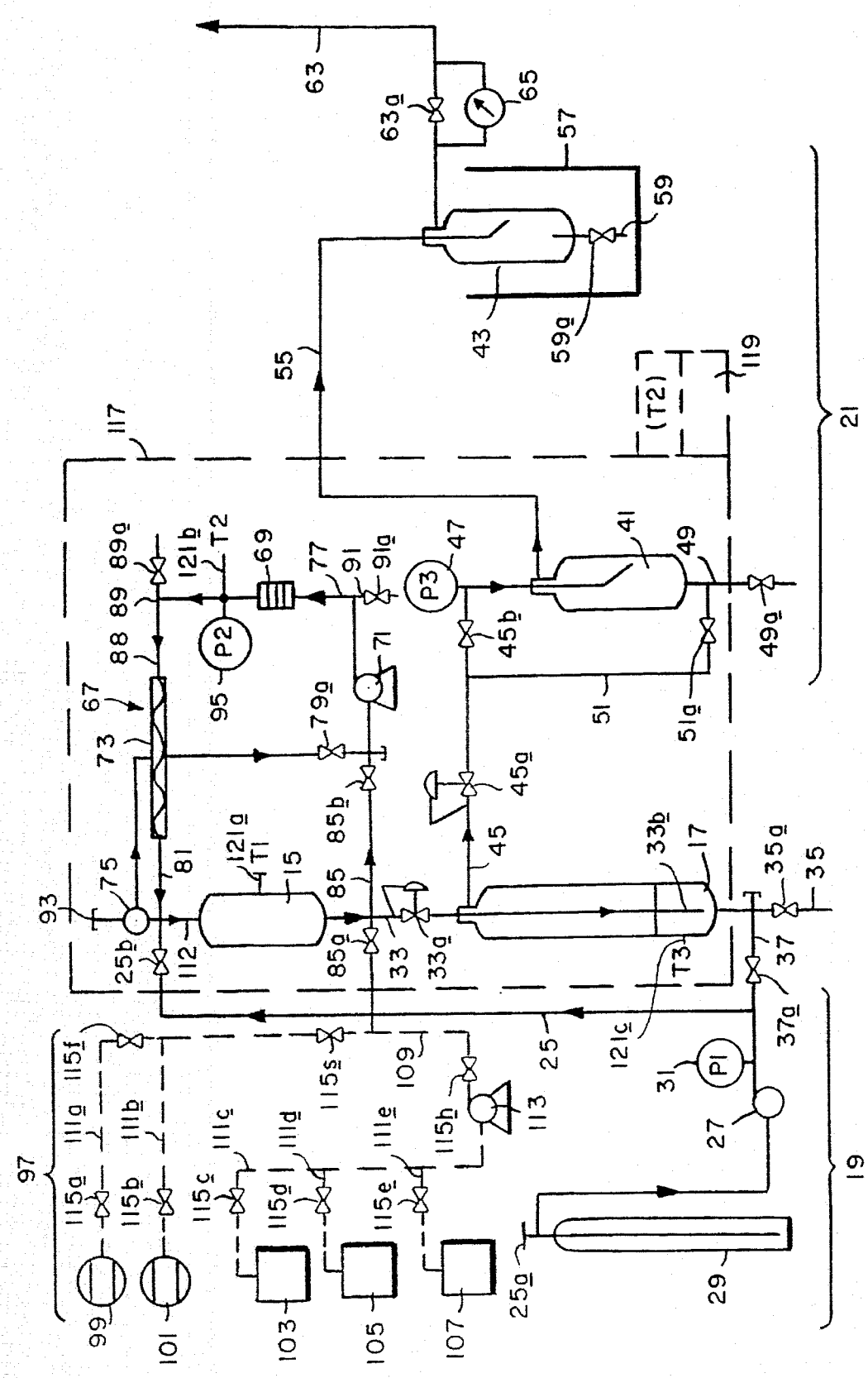
FIG. 1 schematically depicts an apparatus embodying features of the present invention.

One embodiment of the present invention is depicted in FIG. 1. An apparatus for making liposomes, generally designated by the numeral 11 is comprised of the following major elements: a first vessel 15; a second vessel 17; a source of SCoCoNC fluid, generally designated by numeral 19; and a low pressure trap assembly, generally designated by the numeral 21.

First vessel 15 is adapted to receive a supply of one or more of the following articles or compositions; phospholipids, multilamellar vesicles (MLVs), aqueous phases, SCoCoNC fluids, and therapeutic agents.

In one embodiment, first vessel 15 is capable of receiving phospholipids and an aqueous phase. First vessel 15 is in communication with the source of SCoCoNC fluid 19 to receive SCoCoNC fluid, via conduit 25. The term "communication" is used in the sense of being connected to allow fluid to be directed into or out of a vessel, conduit or the like, or to be in contact with.

Conduit 25 is in communication with compressor 27 and storage vessel 29. Storage vessel 29 contains SCoCoNC fluid, which fluid is compelled through conduit 25 by compressor 27. Flow of SCoCoNC fluid through conduit 25 is controlled by valves 25a and 25b. Pressure in conduit 25 is monitored by pressure valve 31.

First vessel 15 receives SCoCoNC fluid from conduit 25, which SCoCoNC fluid forms a mixture with phospholipids and an aqueous phase. First vessel 15 is in communication with second vessel 17 via conduit 33.

Back pressure regulator 33a controls pressure in conduit 33. Back pressure regulator 33a reduces pressure on mixtures flowing through conduit 33, which are received by second vessel 17. In one embodiment, conduit 33 terminates in a nozzle 33b within second vessel 17.

Second vessel 17 is in communication with exit conduit 35. Valve 35a controls the flow of fluid through conduit 35.

Valve 37a controls the flow of fluid in conduit 37. Liposomes which collect in second vessel 17 are withdrawn through exit conduit 35.

Second vessel 17 is in communication with trap assembly 21. Trap assembly 21 is comprised of two major elements: first trap vessel 41 and second trap vessel 43. First trap vessel 41 is in communication with second vessel 17 via conduit 45.

Back pressure regulator 45a controls the pressure in conduit 45. Flow through conduit 45 is controlled by valve 45a. Pressure in conduit 45 is monitored by pressure meter 47.

First trap vessel 41 receives SCoCoNC fluid, and any entrained phospholipids, aqueous phase and liposomes from second vessel 17. Liposomes, phospholipids and aqueous phase are removed from first trap vessel 41 via conduit 49. Valve 49a controls movement of fluids through conduit 49.

Shunt 51 is in communication with conduit 49 and conduit 45. Shunt 51 allows sterilizing and cleaning reagents to be pumped through conduit 49 and back flushed in trap vessel 41. Valve 51a controls the flow of fluids in conduit 51.

First trap vessel 41 communicates with second trap vessel 43 via conduit 55. Second trap vessel 43 provides a second vessel to receive SCoCoNC fluid and any entrained liposomes, phospholipids and aqueous phase, as mixtures flowing from second chamber 17 and first trap vessel 41 during depressurization.

Second trap vessel 43 is maintained in ice bath vessel 57. Ice bath vessel 57 is packed with ice to control and maintain the temperature within second trap vessel 43.

Conduit 59, in communication with second trap vessel 43 allows liposomes and unincorporated phospholipids and aqueous phase to be withdrawn. Valve 59a controls the flow of fluids in conduit 59.

Second trap vessel 43 is in communication with the atmosphere by conduit 63. Flow through conduit 63 is controlled by valve 63a. Flow through conduit 63 is monitored by flow meter 65.

First vessel 15 is in communication with a phospholipid mixing assembly, generally designated by the numeral 67. Phospholipid mixing assembly 67 is comprised of the following major elements: a solids vessel 69, a circulation pump 71, a static in-line mixer 73 and three-way valve 75.

Solids vessel 69 is adapted to receive phospholipids, in solid form, to be solubilized by SCoCoNC fluid. Solids vessel 69 receives SCoCoNC fluid from conduit 77. Conduit 77 is in communication with circulation pump 71. Circulation pump 71 is in communication with three-way valve 75 via conduit 79. Valve 79a controls fluid movement in conduit 79.

Three-way valve 75 is in communication with static in-line mixer 73 via conduit 81. Static in-line mixer 73 is in communication with solids vessel 69 via conduit 83.

Solids vessel 69, circulation pump 71, static in-line mixer 73 and three-way valve 75, of phospholipid mixing assembly 67, define a fluid circuit. The phospholipid mixing assembly 67 is in communication with SCoCoNC fluid storage vessel 29 via conduit 25 which joins conduit 81 between three-way valve 75 and static in-line mixer 73 to allow fluid to be diverted into first chamber 15 and phospholipid mixing assembly 67.

Phospholipid mixing assembly 67 has a vent 89. Valve 89a controls the movement of fluid in vent 89.

Phospholipid mixing assembly 67 has a drain 91 in communication with conduit 77. Valve 91a controls the movement of fluid through drain 91.

Phospholipid mixing assembly 67 has an injection port 93, in communication with three-way valve 75. Injection port 93 allows materials to be injected into first vessel 15 via conduit 112, and into the phospholipid mixing assembly 67.

Phospholipid mixing assembly 67 has a pressure meter 95 in communication with conduit 83. Pressure meter 95 allows the pressure in conduit 83 to be monitored.

First vessel 15, second vessel 17, low pressure trap assembly 21 and phospholipid mixing assembly 67 are in communication with a wash assembly, generally by the numeral 97. Wash assembly 97 is comprised of the following major elements; a source of air 99, a source of water 101, a source of sodium hydroxide 103, a source of hypochlorite solution 105, and a source of methanol 107. Conduit 109 is in communication with each source via conduit branches 111a–e. Conduit 109 is in communication with conduit 25 to allow the wash reagents to enter the first vessel 15, second vessel 17, low pressure trap assembly 21, and phospholipid mixing assembly 67.

Wash reagents, such as water, sodium hydroxide solution, methanol and hypochlorite solutions, are propelled through conduit 109 by pump 113. The flow of fluids in wash assembly 97 is controlled by valves 115a, b, c, d, e, f, j and h.

The first chamber 15 second chamber 17, phospholipid mixing assembly 67, first trap vessel 41 of low pressure assembly 21, and connecting conduits are housed in box 117. Box 117 is heated by heater 119. Heater 119 is controlled by temperature sensor 121b located in conduit 89. Temperature is also sensed by temperature controllers 121a and 121c respectively located on the outside of first chamber 15, and on the outside of second chamber 17.

In operation, cleaning solvents are supplied by pump 113. Pump 113 is a close coupled gear pump rated for 6,000 ml/min against a 100 psia head. The cleaning solvents contained in vessels 101, 103, 105, and 107 included 0.1N NaOH, 10 vol. % hypochlorite solvent, and 95% methanol and deionized water. Deionized water is provided as a flush solvent at a rate of 1,200 ml/min. Instrument compressed air contained in vessel 99 (100 SCFM @100 psig) is used as a displacement and drying solvent.

The system is periodically cleaned by circulating five system volumes each of hypochlorite solution to inactivate any microorganisms present; deionized water, as a flush; caustic, to remove proteins; deionized water, as a flush; methanol, to solubilize lipids; and deionized water, as a flush. The system is blow-dried with compressed air. The apparatus is cleaned between runs by recirculating and then exhausting methanol through the apparatus 11, rinsing the second chamber 17 and low pressure trap assembly 21 with water and then drying with compressed air.

Following cleaning, the apparatus 11 is dried and brought to operating temperature. All valves are placed in a closed position. In its normal operating mode, the solids vessel 69 is first removed from the apparatus, loaded with a known quantity of phosphatidyl choline (PC)/phosphatidyl ethanolamine (PE) mixture and then placed back online in the phospholipid mixing assembly 67. Three way valve 75 is then turned to place injection port 93 in communication with conduit 79. Valve 79a and vent valve 89a are opened.

An optional volume of cosolvent or entrainer, such as ethanol, is then introduced via injection port 93 by means of a hypodermic syringe (not shown). Three way valve 75 is then turned to bring phospholipid mixing assembly 67 in communication with first vessel 15, and the vent valve 89a is closed. Valve 25a is then opened, supplying the SCoCoNC fluid solvent to compressor 27. Compressor 27 is turned on and immediately thereafter valve 25b is opened, introducing the SCoCoNC fluid into first vessel 15 and phospholipid mixing assembly 67. When operating pressure is attained, compressor 27 is turned off and valve 25b is closed.

After system stabilization, pump 71 is turned on and its speed adjusted. With valve 79a opened, pump 71 sucks both the cosolvent from the bottom of the first vessel 15 and the SCoCoNC fluid phase from the top of the first vessel 15. The mixture is then pumped counter-clockwise, mixed by static in-line mixer 73 and directed by three way valve 75 to first vessel 15.

In most cases, an aqueous phase (either deionized distilled water or a buffered solution such as 150 mM saline phosphate buffer at pH=7.0), containing a therapeutic protein is introduced by a hypodermic syringe into the second vessel 17 via sample port 35 and valve 35a.

In the alternative, an aqueous phase may be introduced into first vessel 15 to form a mixture of the aqueous phase and phospholipid dissolved in a SCoCoNC fluid. As a further alternative, MLVs are introduced into first vessel 15 to form a mixture of a SCoCoNC and MLVs. Solution and mixture are introduced with sufficient lead time prior to decompression to allow the solution or mixture to achieve the same temperature as the first vessel 15 and the phospholipid mixing assembly 67.

After mixing pump 71 is turned off, valve 45b, back pressure regulator 45a, valve 63a are fully opened. Back pressure regulator 33a is slowly opened to depressurize first vessel 15 and phospholipid mixing assembly 67. Product is obtained from the second vessel 17, first trap vessel 41, second trap vessel 43 via conduit 35, 49, and 59, respectively. The volume of each collected sample is measured and recorded. Typically, 95% to 100% of the feed (aqueous and cosolvent phases) is recovered in the first trap vessel 41 and none in second trap vessel 43. The collected samples are stored at 4° C.

Other features of the present method and apparatus are exemplified in the following Examples.

EXAMPLE 1

IMPACT OF NOZZLE SIZE AND DESIGN ON THE CRITICAL FLUID FORMATION OF LIPOSOMES

Figure 3A:
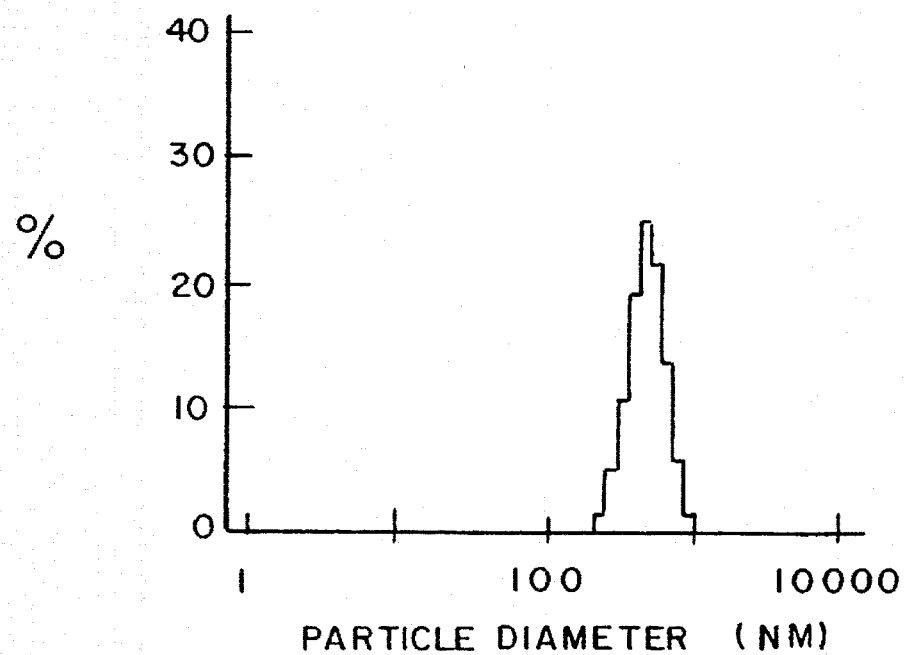
FIG. 3(a) and (b) graphically depicts a particle size analysis of liposomes formed with SCoCoNC fluid carbon dioxide with two nozzle sizes, (a) 0.5 mm and (b) of 0.06 mm FIGS. 4(a) and (b) graphically depicts a particle size analysis of liposomes formed with SCoCoNC fluid nitrous oxide and ethanol with two nozzle sizes, (a) 6.0 mm and (b) 0.22 mm.
Figure 3B:
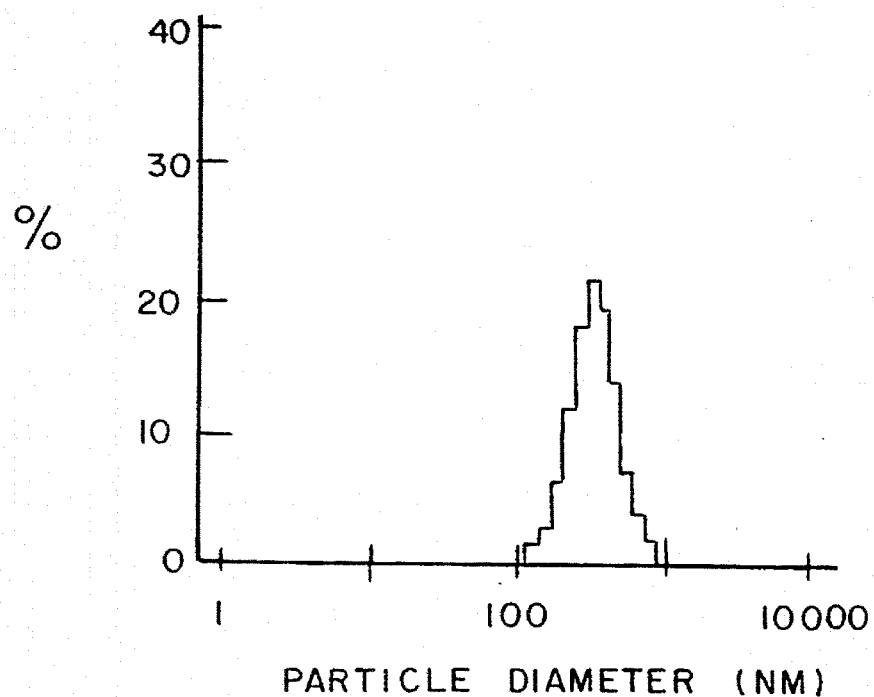

Critical fluid liposomes were formed by first solvating phospholipids in SCoCoNC fluid with/without an entrainer to form a mixture. The mixture was slowly decompressed into an aqueous phase. The number, size and characteristics of critical fluid liposomes formed are governed by a number of parameters such as the size and design of the decompression nozzle, decompressive forces, critical fluid density (temperature and pressure), interfacial forces, charge distribution, and the characteristics of the encapsulated product and the buffer solution. The impact of nozzle size on the critical fluid formation of liposomes in distilled, deionized (DDI) water is listed in Table 1, and shown in FIGS. 3(a) and (b). FIG. 3 graphically depicts particle diameter distribution of liposomes formed by SCoCoNC fluid carbon dioxide with two different nozzles. FIG. 3(a) depicts the distribution of liposomes formed with a nozzle having an interior diameter of 0.50 mm and FIG. 3(b) depicts the distribution of liposomes formed with a nozzle having an interior diameter of 0.06 mm.

TABLE 1

EFFECT OF NOZZLE SIZE ON LIPOSOME DIMENSIONS
(SCF CO2 @ 4,000 psig and 60° C.)

| | | | Particle Size Analysis | | | | |
|---|---|---|---|---|---|---|---|
| | | Nozzle | Sm | | Md | | Lg |
| Exp. No. | SCF | (mm) | (nm) | % | (nm) | % | (nm) | % |
| LIP-14 | CO2 | 0.50 | 0 | 0 | 478 | 100 | 0 | 0 |
| LIP-15 | CO2 | 0.06 | 0 | 0 | 326 | 100 | 0 | 0 |

The liposomes formed with a nozzle diameter of 0.5 millimeters (mm) were readily visible by phase contrast microscopy. Liposomes formed with supercritical fluid carbon dioxide at 4,000 psig and 60° C., had an average size of 478 nanometers (nm). The particle size analysis was done by a size distribution processor (SDP) in a Coulter N4MD laser-based instrument. The SDP allows multimodal size analysis and reports the relative proportion of particles in each discrete size class. The single liposome population had a standard deviation (S.D.) of 180 nm and a 37% coefficient of variance (C.V.).

Liposomes formed with a 0.06 mm ID nozzle were smaller and more uniform, having an average particle size of 326 nm, (a S.D. of 150 nm and a C.V. of 44%). Based on the data in Table 1, the liposome radius appears to depend on nozzle radius to the one fifth power:

$$R'_2 = R'_1 * (r_2/r_1)^{1/5} \qquad (1)$$

where R' is the radius of the liposome formed, r is the inner radius of the tip of the decompression nozzle.

Figure 2:
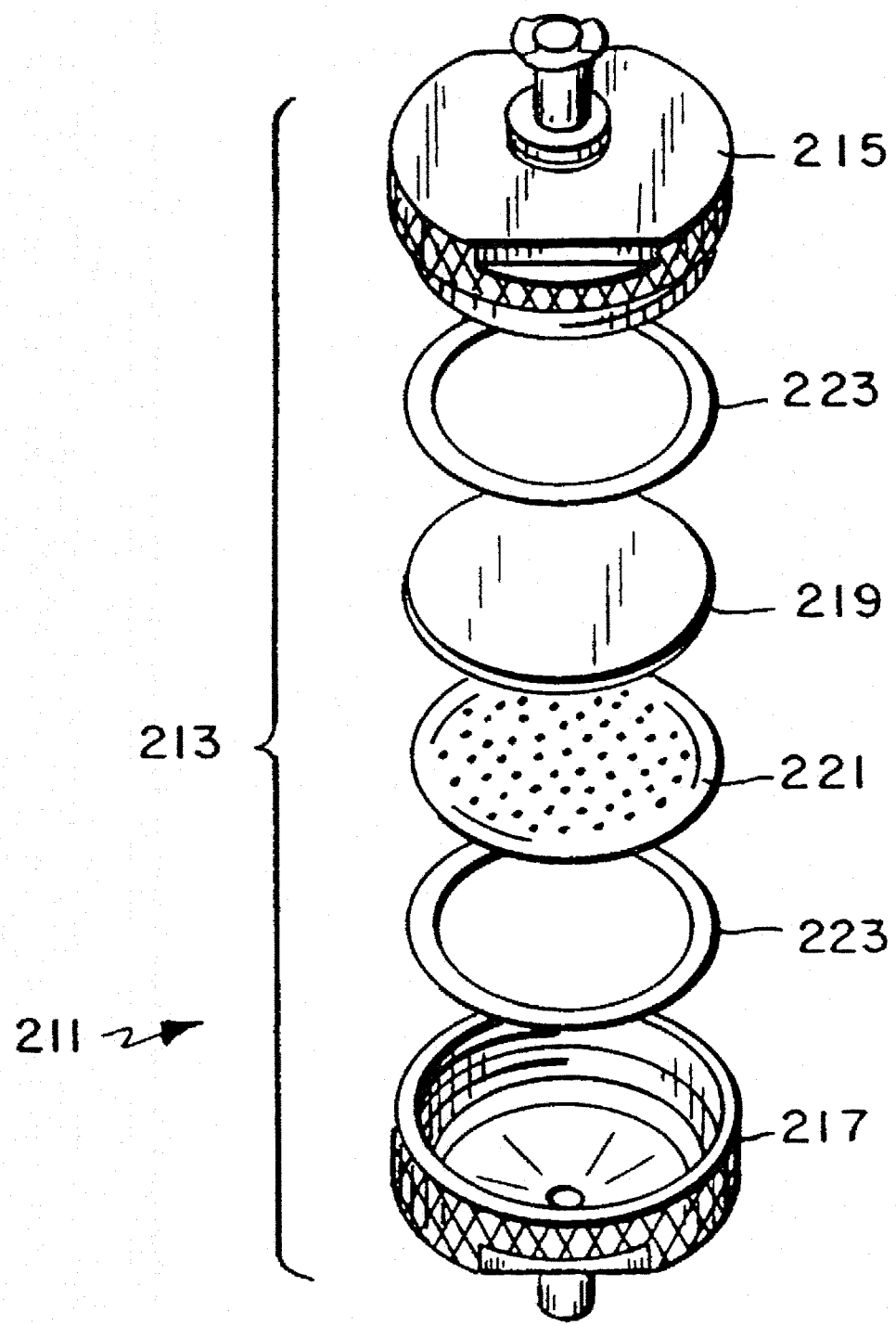
FIG. 2 is an exploded view of a nozzle assembly

In order to further evaluate the impact of nozzle radius on the size of critical fluid liposomes (CFLs), the nozzle design was changed to incorporate a 0.22 micron (um) filter. Turning now to FIG. 2, the filter nozzle assembly, generally designated by the numeral 211 is comprised of the following major elements: a housing 213, comprising a male body 215 and a female body 217; and a filter membrane 219. The filter membrane was retained in housing 213, at the end of conduit 33. Male body 215 and female body 217 fit together by cooperating interfitting threaded sections to form a unitary housing 213. The filter membrane 219 was an inorganic membrane with very uniform and non-tortuous pores (Alltech Associates, Inc., Deerfield, Ill.). The filter membrane 219 was supported by a 316 SS mesh screen 221 and sealed with Teflon O-rings 223.

Figure 4A:
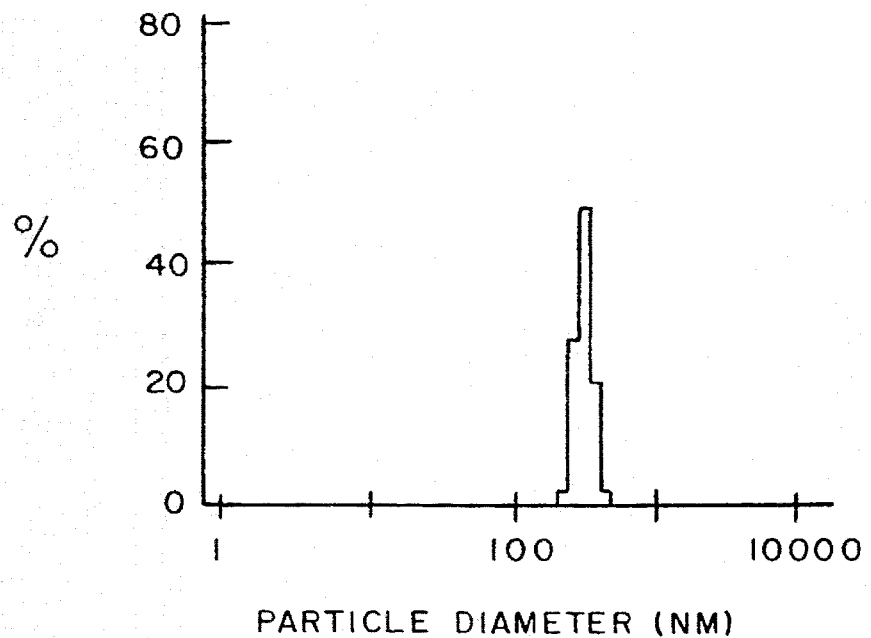
Figure 4B:
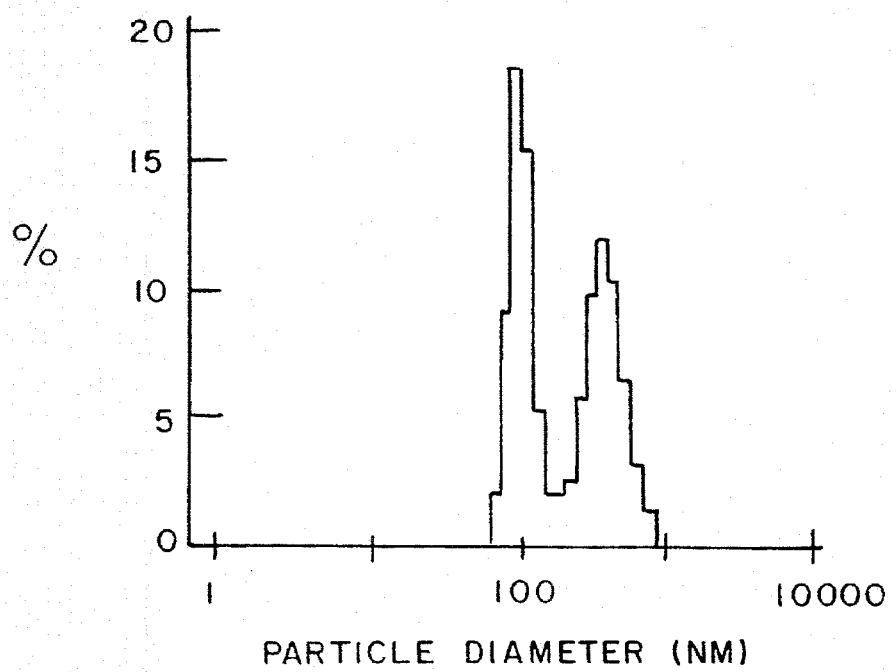

The sizes of liposomes formed by supercritical fluid $N_2O$ through the 0.06 mm needle tip and the 0.22 micron filter paper are listed in Table 2 and shown in FIG. 4. FIG. 4 graphically depicts particle size distribution of liposomes formed with SCoCoNC fluid nitrous oxide and ethanol with two different nozzle sizes. FIG. 4(a) depicts the distribution of liposomes formed with a nozzle of 0.06 mm and FIG. 4(b) depicts the distribution of liposomes formed with a nozzle of 0.22 micron.

TABLE 2

EFFECT OF NOZZLE DESIGN AND SIZE ON LIPOSOME DIMENSIONS (SCF $N_2O$ with Ethanol @ 3,000 psig and 60° C.)

| | | | Particle Size Analysis | | | | | |
|---|---|---|---|---|---|---|---|---|
| Exp. | | | Sm | | Md | | Lg | |
| No. | SCF | Nozzle | (nm) | % | (nm) | % | (nm) | % |
| LIP-53 | N2O/EtOH | 0.06 mm | 0 | 0 | 312 | 100 | 0 | 0 |
| LIP-69 | N2O/EtOH | 0.22 um | 0 | 105 | 50 | 389 | 50 | 0 |

In accordance with Equation 1, LIP-53 liposomes should have been reduced in size from 312 nm to 102 nm in LIP-69. There is at least a 50% agreement between these two experiments and Equation 1 in that the 0.22 micron filter reduced the 0.06 mm critical fluid liposomes by at least 50% to 105 nm.

A 100% size reduction may not have been possible since the 0.22 micron filter has multiple point exits which could allow neighboring bubbles to agglomerate into larger ones. Most of the remaining experiments, unless noted, were conducted with the 0.06 mm orifice.

EXAMPLE 2

IMPACT OF PRESSURE ON THE CRITICAL FLUID FORMATION OF LIPOSOMES

Figure 5:
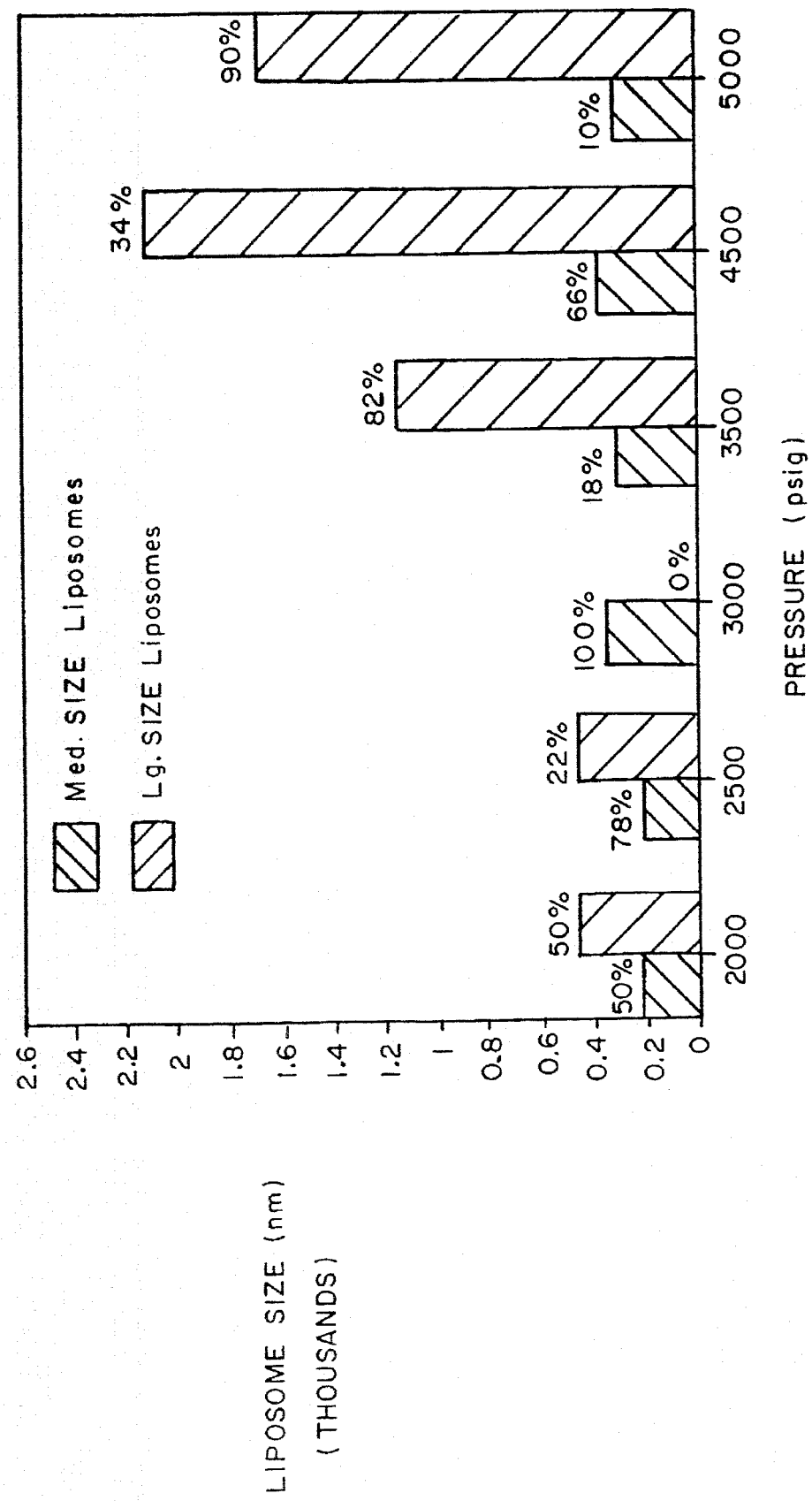
FIG. 5 is a bar graph illustrating the effect of pressure on liposome size.

The effect of critical fluid pressure on the size of liposomes formed by the injection technique is listed in Table 3 and shown as a bar chart in FIG. 5. As illustrated in FIG. 5, for each pressure, the left bar, with lines extending from bottom left to upper right, depicts medium size liposomes (100–400 mm). The right bar, with lines extending from bottom right to upper left, depicts large size liposomes (greater than 400 mm). These CFLs were all formed with the 0.06 mm decompression nozzle.

TABLE 3

EFFECT OF INITIAL CRITICAL FLUID PRESSURE ON LIPOSOME DIMENSIONS
(Critical Fluid $CO_2$ @ 60° C. and 60 mins)

| Exp. No. | Pressure (psig) | Sm (nm) | % | Md (nm) | % | Lg (nm) | % |
|---|---|---|---|---|---|---|---|
| LIP-36 | 2,000 | 0 | 0 | 215 | 50 | 464 | 50 |
| LIP-37 | 2,500 | 0 | 0 | 215 | 78 | 464 | 22 |
| LIP-38 | 3,000 | 0 | 0 | 352 | 100 | 0 | 0 |
| LIP-48 | 3,500 | 0 | 0 | 298 | 18 | 1150 | 82 |
| LIP-41 | 4,500 | 0 | 0 | 372 | 66 | 2110 | 34 |
| LIP-47 | 4,500 | 0 | 0 | 317 | 37 | 1620 | 63 |
| LIP-44 | 5,000 | 0 | 0 | 310 | 10 | 1680 | 90 |

The increase in liposome size with initial decompression pressure is in agreement with the relationship of bubble growth formation pressure. This relationship is, however, complicated by the amount of phospholipids solubilized in the critical fluid phase and the rate of decompression. The former is significant since the most uniformly sized liposomes (100% at 352 nm) were obtained at 3,000 psig, the optimum pressure for solubilizing lecithin in supercritical fluid carbon dioxide at 60° C.

The experiments listed in Table 3 were conducted by circulating the critical fluid for 60 minutes and then slowly decompressing from the listed pressure to atmospheric conditions. The liposomes were thus formed from a variable pressure ranging from an initial pressure of say 5,000 psig to 0 psig in LIP-37.

In order to evaluate the effect of a varying decompression pressure, a series of experiments were conducted in which the liposomes were formed over specific pressure intervals. The results of these experiments are listed in Table 4 below.

TABLE 4

EFFECT OF FRACTIONAL CRITICAL FLUID DEPRESSURIZATION ON LIPOSOME DIMENSIONS

| Exp. No. | Pressure (psig) | Sm (nm) | % | Md (nm) | % | Lg (nm) | % |
|---|---|---|---|---|---|---|---|
| (Critical Fluid $N_2O$ with Ethanol @ 60 C. and 60 mins) | | | | | | | |
| LIP-64 | 3,000–2,000 | 0 | 0 | 244 | 100 | 0 | 0 |
| LIP-65 | 2,000–1,100 | 0 | 0 | 295 | 100 | 0 | 0 |
| LIP-66 | 1,100–0 | 0 | 0 | 337 | 56 | 3,140 | 44 |
| (Critical Fluid $C_2H_4$ with Ethanol @ 60 C. and 60 mins) | | | | | | | |
| LIP-104 | 3,000–2,000 | 0 | 0 | 165 | 100 | 0 | 0 |
| LIP-105 | 2,000–1,000 | 0 | 0 | 183 | 100 | 0 | 0 |
| LIP-106 | 1,000–0 | 0 | 0 | 140 | 76 | 978 | 24 |
| (Critical Fluid $C_3H_8$ with Ethanol @ 60 C. and 60 mins) | | | | | | | |
| LIP-110 | 3,000–2,000 | 0 | 0 | 120 | 62 | 1,430 | 38 |
| LIP-111 | 2,000–1,000 | 0 | 0 | 184 | 28 | 3,160 | 72 |
| LIP-112 | 1,000–0 | 0 | 0 | 136 | 24 | 3,600 | 76 |

For example in LIP-64, SCF N2O with a polar cosolvent at 3,000 psig and 60° C. was contacted with egg yolk lecithin for 60 minutes and then slowly decompressed into DDI water from 3,000 to 2,000 psig and the liposomal solution removed and replaced with fresh DDI water.

In LIP-65, more liposomes were formed by slowly decompressing the remaining critical fluid mixture from 2,000 psig to 1,100 psig.

Finally, in LIP-66, the critical fluid mixture is decompressed from 1,100 psig to atmospheric conditions.

It should be noted that equal volumes of aqueous phases were used in each of the three stages of decompression. The particle size analyses indicate that a unimodal, relatively small distribution of liposomes was formed at pressures above the critical pressure of $N_2O$ which is 1,040 psig. A significant fraction of larger liposomes are formed in decompressing from 1,000 psig to atmospheric conditions. Similar fractional decompression effects on liposome size are shown in Table 4 for ethylene/ethanol and propane/ethanol mixtures.

It should be noted that the fractional nitrous oxide/ethanol decompression series was conducted with chicken egg yolk lecithin and a 0.06 mm decompression nozzle; the remaining decompression series in Table 4 were conducted with pure phosphatidyl choline in ethanol with a 0.5 mm decompression nozzle. The larger liposomes in the last stage of fractional decompression are probably formed because the density of the critical fluid changes rapidly below the critical pressure.

Operationally, decompression takes much longer at pressures around and below the critical pressure in order to retain the DDI water or aqueous buffer solution in the decompression chamber; also, the discharge volume of gas increases dramatically. This rapid increase in gas volume probably results in the formation of larger bubble and liposomes because of Joule-Thompson cooling effects due to gas expansion. The LIP-112 sample listed in Table 4 was in fact frozen after the third stage of propane/ethanol fractional decompression.

EXAMPLE 3

IMPACT OF CRITICAL FLUID TYPE ON THE CRITICAL FLUID FORMATION OF LIPOSOMES

Figure 6:
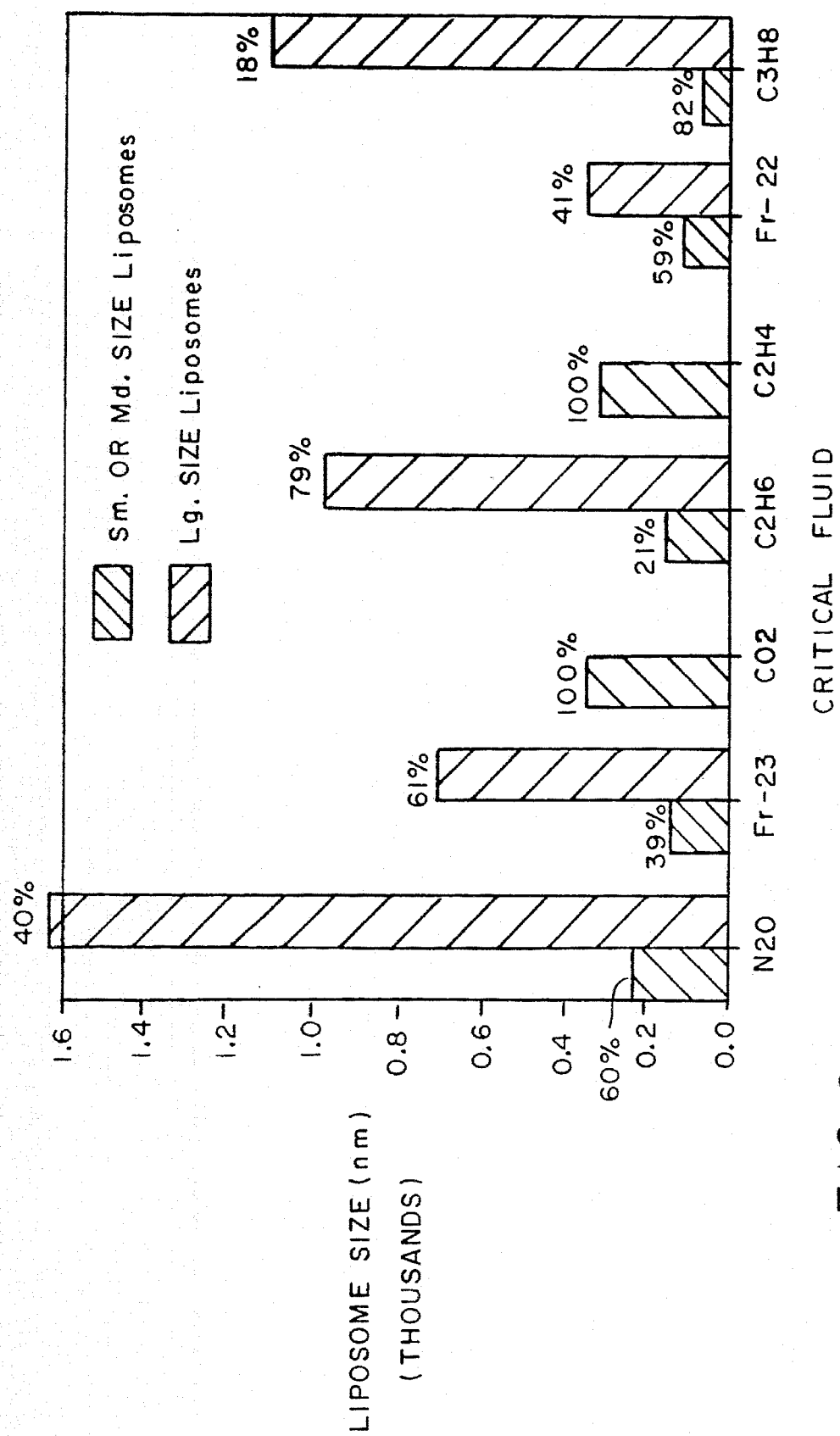
FIG. 6 is a bar graph illustrating the effect of critical fluid type on liposome size.

Liposomes formed by several critical fluids are characterized in terms of particle size distributions in Table 5 and compared by bar charts in FIG. 6. As illustrated in FIG. 6, for each critical fluid, the left bar, with lines extending upward from bottom left to upper right, reflect small to medium sized liposomes. The right bar, with lines extending upward from bottom right to upper left, reflect large liposomes. These experiments were all conducted by contacting chicken egg yolk lecithin with the critical fluid phase (without cosolvents) at 3,000 psig and 60° C. for 60 minutes, and then slowly decompressing through the 0.06 mm decompression nozzle.

TABLE 5

EFFECT OF CRITICAL FLUID TYPE ON LIPOSOME DIMENSIONS
(Critical Fluid @ 3,000 psig and 60° C. for 60 mins)

| | | Particle Size Analysis | | | | |
|---|---|---|---|---|---|---|
| | | Sm | | Md | | Lg |
| Exp. No. | SCF | (nm) | % | (nm) | % | (nm) | % |
| LIP-51 | N$_2$O | 0 | 0 | 233 | 60 | 4,370 | 40 |
| LIP-61 | Fr-23 | 0 | 0 | 143 | 39 | 705 | 61 |
| LIP-38 | CO$_2$ | 0 | 0 | 352 | 100 | 0 | 0 |
| LIP-62 | C$_2$H$_6$ | 0 | 0 | 152 | 21 | 980 | 79 |
| LIP-63 | C$_2$H$_4$ | 0 | 0 | 320 | 100 | 0 | 0 |
| LIP-60 | Fr-22 | 106 | 59 | 348 | 41 | 0 | 0 |
| LIP-55 | C$_3$H$_8$ | 57 | 82 | 0 | 0 | 1,050 | 18 |
| LIP-56 | C$_3$H$_8$ | 57 | 82 | 0 | 0 | 1,100 | 18 |

Supercritical ethylene in LIP-63 created a unimodal albeit broad distribution (an average particle size of 320 nm and a S.D. of 300 nm) of liposomes. Decompression at subcritical pressures could have resulted in bimodal distributions for the remaining critical fluids tested.

EXAMPLE 4

IMPACT OF POLAR ENTRAINER OR COSOLVENT ON THE CRITICAL FLUID FORMATION OF LIPOSOMES

In general, polar entrainers control the size and uniformity of critical fluid liposomes as shown in Table 6 below:

TABLE 6

EFFECT OF POLAR COSOLVENTS ON NITROUS OXIDE CFLs
(SCF N2O @ 3,000 psig and 60° C. for 60 mins)

| | | Particle Size Analysis | | | | |
|---|---|---|---|---|---|---|
| | | Sm | | Md | | Lg |
| Exp. No. | Cosolvent | (nm) | % | (nm) | % | (nm) | % |
| LIP-51 | None | 0 | 0 | 233 | 60 | 4,370 | 40 |
| LIP-53 | Ethanol | 0 | 0 | 312 | 0 | 0 | 0 |
| LIP-52 | Methanol | 88 | 52 | 338 | 42 | 0 | 0 |
| LIP-54 | Acetone | 91 | 47 | 311 | 53 | 0 | 0 |

The micron sized liposome population in LIP-51, SCF N$_2$O without a polar cosolvent, was most probably formed during decompression below nitrous oxide's critical point. The addition of 2 vol % ethanol in LIP-53 produces a narrow, unimodal distribution of liposomes having an average size of 312 nm, a standard deviation of 54 nm and a 17% coefficient of variance. Likewise, 2 vol % methanol in LIP-52 and 2 vol % acetone in LIP-54 caused the elimination of the micron sized liposome population. These two additives did, however, form distributions with average sizes around 100 nm and 300 nm. Both distributions are relatively narrow for SCF N$_2$O with these two polar cosolvents. The added polar entrainers are most likely controlling the size of the nitrous oxide CFLs by lowering the interfacial tension between the nitrous oxide and water (5% ethanol in water reduces surface tension from 72 dynes/cm at 25° C. to 53 dynes/cm; 5% acetone in water reduces the surface tension to 56 dynes/cm). A low, more uniform interfacial tension will control the size of the bubbles and the liposomes formed. The enhanced solubility of lecithin in SCF N$_2$O with polar entrainers could also be responsible for the reduction in the sizes and distributions of the CFLs.

Polar entrainers have a similar impact on CFLs formed by near critical propane as suggested in Table 7. The addition of a 2 vol % ethanol cosolvent eliminates the micron sized liposome population formed with near critical propane, and creates a single liposome population having an average size of 196 nm and a standard deviation of 300 nm. This elimination and size reduction is probably caused by the alteration of propane-water interfacial properties since, lecithin is very soluble in near critical propane by itself. The sizes of CFLs do also depend on the buffers used and the proteins to be encapsulated. Acetone has a very dramatic impact on propane CFLs, reducing the liposomes to a single population with an average size of 85 nm and a standard deviation of 83 nm. It is quite possible that methanol did not exhibit a similar impact because of the presence of salt (0.09M NaCl) in LIP-76.

TABLE 7

EFFECT OF POLAR COSOLVENTS ON PROPANE CFLs
(Near Critical C3H8 @ 3,000 psig and 60° C. for 60 mins)

| | | Particle Size Analysis | | | | |
|---|---|---|---|---|---|---|
| | | Sm | | Md | | Lg |
| Exp. No. | Cosolvent | (nm) | % | (nm) | % | (nm) | % |
| LIP-56 | None | 57 | 82 | 0 | 0 | 1,100 | 18 |
| LIP-59 | Ethanol | 0 | 0 | 196 | 0 | 0 | 0 |
| LIP-76* | Methanol | 62 | 24 | 0 | 0 | 5,720 | 76 |
| LIP-77** | Acetone | 85 | 100 | 0 | 0 | 0 | 0 |

*Liposomes formed in a saline phosphate buffer with cytochrome-C.
**Liposomes formed in a phosphate buffer with cytochrome-C.

There appears to be little or no impact of polar cosolvents on liposomes formed by FREON-22 as shown in Table 8. It should, however, be noted that these three experiments were conducted at different pressures—LIP-60 at 3,000 psig, LIP-73 at 4,000 psig and LIP-75 at 5,000 psig. Initial pressure may have a significant influence on liposome size and distribution.

TABLE 8

EFFECT OF POLAR COSOLVENTS ON FREON-22 CFLs
(Near Critical CHClF2 @ 60° C. for 60 mins)

| | | Particle Size Analysis | | | | |
|---|---|---|---|---|---|---|
| | | Sm | | Md | | Lg |
| Exp. No. | Cosolvent | (nm) | % | (nm) | % | (nm) | % |
| LIP-60 | None | 106 | 59 | 348 | 41 | 0 | 0 |
| LIP-73 | Ethanol | 118 | 76 | 531 | 24 | 0 | 0 |
| LIP-75 | Methanol | 84 | 66 | 473 | 34 | 0 | 0 |

EXAMPLE 5

IMPACT OF MODE OF OPERATION ON THE CRITICAL FLUID FORMATION OF LIPOSOMES

Size distributions of liposomes formed by the critical fluid injection and decompression techniques are compared and listed in Table 9.

TABLE 9

EFFECT OF OPERATIONAL MODE ON CRITICAL FLUID LIPOSOMES
($C_2H_4$/EtOH @ 3,000 psig and 60° C. for 60 mins)

| | | Particle Size Analysis | | | | |
|---|---|---|---|---|---|---|
| | | Sm | | Md | | Lg |
| Exp. No. | Mode | (nm) | % | (nm) | % | (nm) | % |
| LIP-98 | Decompression | 11 | 87 | 83 | 11 | 384 | 1 |
| LIP-99 | Injection | 0 | 0 | 63 | 90 | 1,780 | 10 |

Both experiments listed in Table 9 were conducted with a 150 mM saline phosphate buffer containing 1 mg/ml cytochrome-C and 9.1 mg/ml of chicken egg yolk lecithin. Also, a slow decompression rate of approximately 1,000 psi/min was maintained through a 0.06 mm nozzle tip for both experiments. The data in Table 9 suggests that critical fluid decompression results in a smaller particle size distribution than the critical fluid injection technique.

The effect of decompression rate on the size distribution of liposomes formed by the critical fluid decompression technique is compared in Table 10. Both experiments were conducted with identical concentrations of protein and lecithin in a saline phosphate buffer with a 0.50 mm nozzle tip. The data suggests that rapid decompression (approximately 1,000 psi/sec) does not significantly impact liposome size; in fact, slow decompression (approximately 1,000 psi/min) appears to offer good control in that a small (mean size of 92 nm), unimodal distribution was obtained in LIP-100.

TABLE 10

EFFECT OF RATE ON LIPOSOMES FORMED BY CRITICAL FLUID DECOMPRESSION
(C2H4/EtOH @ 3,000 psig and 60° C. for 60 mins)

| | | Particle Size Analysis | | | | |
|---|---|---|---|---|---|---|
| | Decompression | Sm | | Md | | Lg |
| Exp. No. | Rate | (nm) | % | (nm) | % | (nm) | % |
| LIP-9 | Rapid | 82 | 87 | 0 | 0 | 2,980 | 13 |
| LIP-100 | Slow | 92 | 100 | 0 | 0 | 0 | 0 |

EXAMPLE 5

ENCAPSULATION CHARACTERISTICS OF LIPOSOMES

Encapsulation protocols are typically "passive" in that they rely on the ability of liposomes to capture a certain aqueous volume during vesicle formation. As a result, trapping efficiencies can vary dramatically, ranging from less than 1% for small unilamellar vesicles (SUVs) to as high as 88% for some multilamellar vesicles (MLVs). Entrapment efficiencies are a function of size and nature of the method (and thus liposome manufacturing technique).

Liposomes can also be loaded by relying on their ability to sequester certain drugs in response to transmembrane ion gradients. This "active" protocol, also referred to as remote loading, involves the uptake of charged amphipathic drugs into preformed liposomes which have a transmembrane pH gradient (low intraliposomal pH when the drug involved is ionic) or a transmembrane potential gradient with exogenous ionophores such as potassium ion. For example, trapping efficiencies of 98% and drug:lipid ratios as high as 1:2.2 (w/w) can be readily achieved for doxorubicin hydrochloride in a LUV system (Mayer et al., 1985). Unlike the "passive" protocol, trapping efficiency is independent of lipid concentration. Transmembrane ion gradients not only accomplish efficient drug encapsulation but also decrease the rate of drug efflux from the vesicles as much as 30-fold.

An alternate method of obtaining high trapping efficiencies and high drug:lipid ratios is to chemically attach a hydrophobic group (e.g. a fatty acid or phospholipid) to the drug; this creates a molecule that is highly soluble in the liposome membrane. Liposomes made with SCoCoNC fluids can be loaded with a desired composition in any manner which would apply to liposomes made by conventional techniques. The loading of cytochrome-C in liposomes formed by sonication and critical fluids is summarized in Table 11. The loading was passive in the sense that cytochrome-C was present in the aqueous phase during the formation of the liposome.

TABLE 21

SIZE AND TRAPPING EFFICIENCIES OF CRITICAL FLUID LIPOSOMES
(Critical fluids @ 3,000 psig and 60° C. for 60 mins)

| | | Lipid Conc. | Particle Size Analysis | | | | | | Trapping Efficiency |
|---|---|---|---|---|---|---|---|---|---|
| | | | Sm | | Md | | Lg | | |
| Exp. No. | SCF | (mg/ml) | (nm) | % | (nm) | % | (nm) | % | (%) |
| LIP-96 | Sonication | 10.0 | 11 | 85 | 97 | 15 | 0 | 0 | 13.5 |
| LIP-97 | C2H4/EtOH | 9.1 | 82 | 87 | 0 | 0 | 2,980 | 13 | 14.9 |
| LIP-98 | C2H4/EtOH | 9.1 | 11 | 87 | 83 | 11 | 384 | 1 | 12.9 |

TABLE 21-continued

SIZE AND TRAPPING EFFICIENCIES
OF CRITICAL FLUID LIPOSOMES
(Critical fluids @ 3,000 psig and 60° C. for 60 mins)

| | | | Particle Size Analysis | | | | | Trapping |
| | | Lipid Conc. | Sm | | Md | | Lg | | Efficiency |
| Exp. No. | SCF | (mg/ml) | (nm) | % | (nm) | % | (nm) | % | (%) |
| --- | --- | --- | --- | --- | --- | --- | --- | --- | --- |
| LIP-99 | C2H4/EtOH | 9.1 | 63 | 90 | 0 | 0 | 1,780 | 10 | 14.0 |
| LIP-85 | C3H8/EtOH | 16.6 | 0 | 0 | 166 | 54 | 998 | 46 | 27.7 |
| LIP-87 | C3H8/EtOH | 3.9 | 88 | 17 | 0 | 0 | 3,690 | 83 | 18.5 |
| LIP-89 | N2O/EtOH | 3.9 | 97 | 33 | 384 | 6 | 3,000 | 61 | 33.3 |

EXAMPLE 7

STABILITY OF CRITICAL FLUID LIPOSOMES

Stability of critical fluid liposomes, and of liposomes in general, will depend on a variety of parameters such as raw material composition, purity and oxygen susceptibility, end product sterility, compatibility between encapsulated drug and liposomal materials, aqueous phase pH and ionic strength and composition, and preparation technique. Lack of stability will impact liposome size and drug retention capability. For pharmaceutical applications, liposomal formulations are desirable to have a shelf-life between 6 to 24 months at 4° C.

Liposomes are subject to massive fusion and leakage during conventional freeze-drying and rehydration. By coating each side of the lipid membrane with equimolar concentrations of sugars such as glucose, free-flowing powdered liposomal preparations can be formed that retain 90% or more of the entrapped materials with no change in size of the liposomes (Crowe et al., 1985). Stability problems can also be avoided by "remote loading" preformed liposomes at the time of use (Bally et al., 1985). Remote loading can be readily accomplished by changing the pH of a preformed liposomal preparation in order to create a transmembrane pH gradient prior to adding the therapeutic drug in the required dosage. Reproducible and complete uptake of the drug is achieved within five minutes, resulting in an injectable liposomal formulation (Ostro et al., 1989). Stability of liposomal formulations can also be increased by using synthetic saturated lipids or by adding antioxidants such as alpha-tocopherol and Beta-hydroxytoluene to prevent phospholipid degradation.

The stability of critical fluid liposomes was examined in order to evaluate if critical fluids enhanced or decreased the stability of liposomal formulations. This examination was conducted by measuring the particle size distribution as a function of time. No special precautions, such as preparation of critical fluid liposomes under a blanket of inert gas, the use of antioxidants, or aseptic processing and collecting procedures were utilized in the preparation of critical fluid liposomes. The time stability of critical fluid liposomal formulations are listed in Table 12.

TABLE 12

IMPACT OF NOZZLE SIZE ON TIME STABILITY
OF CRITICAL FLUID LIPOSOMES
(SCF CO2 @ 4,000 psig and 60° C.)

| | Elapsed | | Particle Size Analysis | | | | | |
| | Time | Nozzle | Sm | | Md | | Lg | |
| Exp. No. | (days) | (mm) | (nm) | % | (nm) | % | (nm) | % |
| --- | --- | --- | --- | --- | --- | --- | --- | --- |
| LIP-14 | 18 | 0.50 | 0 | 0 | 478 | 100 | 0 | 0 |
| LIP-14 | 52 | 0.50 | 0 | 0 | 509 | 100 | 0 | 0 |
| LIP-14 | 187 | 0.50 | 0 | 0 | 316 | 41 | 1,810 | 59 |
| LIP-15 | 6 | 0.06 | 0 | 0 | 326 | 100 | 0 | 0 |
| LIP-15 | 52 | 0.06 | 0 | 0 | 312 | 100 | 0 | 0 |
| LIP-15 | 187 | 0.06 | 0 | 0 | 315 | 100 | 0 | 0 |

Supercritical carbon dioxide liposomes exhibit good to excellent stability at a storage temperature of 4° C. over a six (6) month period as shown by the data in Table 12.

The smaller diameter liposomes, formed by the 0.06 mm nozzle, appear to be more stable than the larger liposomes formed by the 0.50 mm nozzle.

As a second point of comparison for critical fluid liposomes, the relative stability of liposomes formed by sonic energy can be inferred from the listing in Table 13.

TABLE 13

STABILITY OF LIPOSOMES FORMED BY
SONIC ENERGY
(10 minutes @ 60° C.)

| | | Elapsed | Particle Size Analysis | | | | | |
| Exp. | | Time | Sm | | Md | | Lg | |
| No. | Buffer | (days) | (nm) | % | (nm) | % | (nm) | % |
| --- | --- | --- | --- | --- | --- | --- | --- | --- |
| LIP-91 | DDI | 1 | 22 | 100 | 0 | 0 | 0 | 0 |
| LIP-91 | DDI | 23 | 28 | 93 | 97 | 7 | 0 | 0 |
| LIP-95 | PBS | 1 | 61 | 100 | 0 | 0 | 0 | 0 |
| LIP-95 | PBS | 24 | 40 | 90 | 216 | 10 | 0 | 0 |
| LIP-96 | PBS/Cytochrome-C | 1 | 11 | 85 | 97 | 15 | 0 | 0 |
| LIP-96 | PBS/Cytochrome-C | 24 | 0 | 0 | 109 | 79 | 956 | 21 |

The liposomes formed by sonic energy in deionized distilled (DDI) water exhibit a small amount of agglomeration after twenty three (23) days of storage at 4° C.

The time stability of liposomes formed by other critical fluids over a four (4) month period are presented in Table 14.

The data indicates that the most effective critical fluids, in order of decreasing stability, were: (1) propane; (2) FREON-22; (3) nitrous oxide; (4) ethane; (5) FREON-23; and (6) ethylene.

TABLE 14

EFFECT OF CRITICAL FLUID TYPE ON
TIME STABILITY OF CRITICAL FLUID LIPOSOMES.
(Critical Fluid @ 3,000 psig and 60° C. for 60 mins)

| Exp. No. | SCF | Elapsed Time (days) | Intensity Particle Size Analysis | | | | | |
|---|---|---|---|---|---|---|---|---|
| | | | Sm (nm) | % | Md (nm) | % | Lg (nm) | % |
| LIP-51 | $N_2O$ | 1 | 0 | 0 | 233 | 60 | 4,370 | 40 |
| LIP-51 | $N_2O$ | 124 | 0 | 0 | 189 | 76 | 1,780 | 24 |
| LIP-61 | Fr-23 | 1 | 0 | 0 | 143 | 39 | 705 | 61 |
| LIP-61 | Fr-23 | 117 | 29 | 81 | 278 | 19 | 0 | 0 |
| LIP-62 | $C_2H_6$ | 1 | 0 | 0 | 152 | 21 | 980 | 79 |
| LIP-62 | $C_2H_6$ | 114 | 0 | 0 | 294 | 100 | 0 | 0 |
| LIP-63 | $C_2H_6$ | 1 | 0 | 0 | 320 | 100 | 0 | 0 |
| LIP-63 | $C_2H_6$ | 114 | 0 | 0 | 238 | 38 | 10,000 | 62 |
| LIP-60 | Fr-22 | 1 | 106 | 59 | 348 | 41 | 0 | 0 |
| LIP-60 | Fr-22 | 117 | 138 | 73 | 521 | 27 | 0 | 0 |
| LIP-56 | $C_3H_8$ | 1 | 57 | 82 | 0 | 0 | 1,100 | 18 |
| LIP-56 | $C_3H_8$ | 119 | 50 | 89 | 0 | 0 | 772 | 11 |

In general, polar cosolvents improved the stability of critical fluid liposomes. This improvement is exemplified in Table 15 which shows that the stability of critical nitrous oxide liposomes is much better with methanol as an additive; both ethanol and acetone additives are better than none and have a similar impact on the stability of $N_2O$ critical fluid liposomes.

TABLE 15

EFFECT OF POLAR COSOLVENTS ON TIME
STABILITY OF CRITICAL FLUID LIPOSOMES
(SCF $N_2O$ @ 3,000 psig and 60° C. for 60 mins)

| Exp. No. | Co-Solvent | Elapsed Time (days) | Particle Size Analysis | | | | | |
|---|---|---|---|---|---|---|---|---|
| | | | Sm (nm) | % | Md (nm) | % | Lg (nm) | % |
| LIP-51 | None | 1 | 0 | 0 | 233 | 60 | 4,370 | 40 |
| LIP-51 | None | 7 | 33 | 49 | 317 | 49 | 4,090 | 22 |
| LIP-51 | None | 124 | 0 | 0 | 189 | 76 | 1,780 | 24 |
| LIP-53 | Ethanol | 1 | 0 | 0 | 312 | 0 | 0 | 0 |
| LIP-53 | Ethanol | 7 | 0 | 0 | 297 | 100 | 0 | 0 |
| LIP-53 | Ethanol | 123 | 98 | 53 | 317 | 47 | 0 | 0 |
| LIP-52 | Methanol | 1 | 88 | 52 | 338 | 42 | 0 | 0 |
| LIP-52 | Methanol | 7 | 88 | 58 | 312 | 42 | 0 | 0 |
| LIP-52 | Methanol | 123 | 97 | 62 | 345 | 38 | 0 | 0 |
| LIP-54 | Acetone | 1 | 91 | 47 | 311 | 53 | 0 | 0 |
| LIP-54 | Acetone | 7 | 100 | 47 | 332 | 53 | 0 | 0 |
| LIP-54 | Acetone | 123 | 0 | 0 | 311 | 100 | 0 | 0 |

Embodiments of the present invention allow the recovery of raw materials, lipids and solvents which are not incorporated into the final liposome product. Embodiments of the present invention feature efficient drug entrapment and recovery of unencapsulated drugs. The operating parameters of the apparatus and method are consistent with other industrially applied processes. The method and apparatus are capable of operating continuously.

Thus, while preferred embodiments of the invention have been described, the present invention is capable of variation and modification and, therefore, the present invention should not be limited to the precise details set forth, but should include such changes and alterations as fall within the purview of the following claims.

What is claimed is:

1. A method of making liposomes comprising:
   a) forming a solution or mixture of a phospholipid and an aqueous phase in a critical, supercritical or near critical fluid said solution or mixture being at a pressure of at least 1,000 psig;
   b) reducing the pressure of the solution or mixture to separate the critical, supercritical or near critical fluid from the phospholipid and aqueous phase, said phospholipid and aqueous phase forming one or more liposomes.

2. The method of claim 1 wherein said liposome has a therapeutic agent.

3. The method of claim 2 wherein said therapeutic agent is a peptide.

4. The method of claim 1 wherein said aqueous phase has a therapeutic agent.

5. The method of claim 1 wherein said phospholipid has a therapeutic agent.

6. The method of claim 1 further comprising the step of actively loading a therapeutic agent into said liposome.

7. The method of claim 1 wherein said critical, supercritical, or near critical fluid is selected from the group of compounds capable of forming critical fluid consisting of carbon dioxide, nitrous oxide, propane, ethylene and ethane.

8. The method of claim 1 wherein said mixture or solution is decompressed as the mixture or solution exits a nozzle.

9. The method of claim 8 wherein said nozzle has one or more openings which opening has a diameter ranging from approximately 0.5 to 0.6 microns.

10. The method of claim 1 wherein said critical, supercritical or near critical fluid comprises entrainers.

11. The method of claim 10 wherein said entrainers are selected from the group of compounds consisting of methanol, ethanol and acetone.

12. A method of making liposomes comprising:
   a) forming a solution or mixture of a phospholipid and a critical, supercritical or near critical fluid said solution or mixture being at a pressure of at least 1,000 psig;
   b) injecting said solution or mixture into an aqueous phase to form one or more liposomes.

13. The method of claim 12 further comprising the step of decompressing the solution or mixture as said solution or mixture is injected.

14. The method of claim 12 wherein said liposome has a therapeutic agent.

15. The method of claim 14 wherein said therapeutic agent is a peptide.

16. The method of claim 12 wherein said aqueous phase contains a therapeutic agent.

17. The method of claim 12 wherein said phospholipid has a therapeutic agent.

18. The method of claim 12 further comprising the step of actively loading a therapeutic agent into the liposomes formed.

19. The method of claim 12 wherein said solution or mixture is injected into said aqueous phase through a nozzle.

20. The method of claim 19 wherein said nozzle has at least one opening having a diameter in the range of approximately 0.5 to 0.6 microns.

21. The method of claim 12 wherein said critical, supercritical or near critical fluid is selected from the group of compounds capable of forming critical fluids consisting of carbon dioxide, nitrous oxide, halo-hydrocarbons, propane, ethylene, and ethane.

22. The method of claim 12 wherein said critical, supercritical or near critical fluid further comprises entrainers.

23. The method of claim 21 wherein said entrainer is selected from the group of compounds consisting of methanol, ethanol, and acetone.

24. A method of making liposomes comprising:
   a) forming a mixture of multilamellar vesicles and a critical, supercritical or near critical fluid said mixture being at a pressure of at least 1,000 psig; and
   b) reducing the pressure of the mixture to remove said critical, supercritical or near critical fluid, whereby said multilamellar vesicles form one or more liposomes.

25. The method of claim 24 further comprising the step of forming said multilamellar vesicles by hydrating phospholipids in an aqueous phase.

26. The method of claim 24 wherein said multilamellar vesicle has a therapeutic agent.

27. The method of claim 26 wherein said therapeutic agent is a peptide.

28. The method of claim 24 further comprising the step of actively loading a therapeutic agent into said liposome.

29. The method of claim 24 comprising the step of controlling the rate of pressure reduction to form liposomes of predetermined size.

30. An apparatus for making liposomes comprising:
   a) a first vessel for forming a solution or mixture of one or more of the following, a phospholipid, an aqueous phase, and multilamellar vesicles, and a critical, supercritical or near critical fluid;
   b) decompression means in fluid communication with said first vessel for receiving said solution or mixture and reducing the pressure of said solution or mixture to separate the critical, supercritical or near critical fluid from the phospholipids, aqueous phase, and multilamellar vesicles, said phospholipid and aqueous phase and said multilamellar vesicles forming one or more liposomes, wherein said apparatus comprises a phospholipid and critical, supercritical, or near critical fluid mixing circuit, in communication with said first vessel, said mixing circuit for receiving phospholipid and critical, supercritical, or near critical fluid, mixing said phospholipid and critical, supercritical or near critical fluid and directing said mixture into said first vessel.

31. The apparatus of claim 30 wherein said mixing circuit comprises a static mixer, a phospholipid vessel and pump means, said pump means in communication with said static mixer and phospholipid vessel, said pump means receiving critical, supercritical or near critical fluid and pumping said critical, supercritical or near critical fluid into said phospholipid vessel, said phospholipid vessel in communication with said pump and static mixer, said phospholipid vessel for containing phospholipid and receiving critical or near critical fluid, and directing said phospholipid and critical fluid, supercritical or near critical fluid to said static mixer, said static mixer in communication with said phospholipid vessel and said first vessel for receiving critical, supercritical or near critical fluid and phospholipid to form a mixture which mixture is directed into said first vessel.

* * * * *